US010064765B2

(12) United States Patent
Takino

(10) Patent No.: US 10,064,765 B2
(45) Date of Patent: Sep. 4, 2018

(54) WEARING ARTICLE

(75) Inventor: Shunsuke Takino, Kagawa (JP)

(73) Assignee: Unicharm Corporation, Ehime (JP)

( * ) Notice: Subject to any disclaimer, the term of this patent is extended or adjusted under 35 U.S.C. 154(b) by 822 days.

(21) Appl. No.: 13/519,624

(22) PCT Filed: Dec. 16, 2010

(86) PCT No.: PCT/JP2010/072643
§ 371 (c)(1),
(2), (4) Date: Jun. 28, 2012

(87) PCT Pub. No.: WO2011/081026
PCT Pub. Date: Jul. 7, 2011

(65) Prior Publication Data
US 2013/0012906 A1 Jan. 10, 2013

(30) Foreign Application Priority Data
Dec. 28, 2009 (JP) .................................. 2009-297996

(51) Int. Cl.
A61F 13/494 (2006.01)
A61F 13/496 (2006.01)

(52) U.S. Cl.
CPC ...... A61F 13/49466 (2013.01); A61F 13/496 (2013.01)

(58) Field of Classification Search
CPC .......... A61F 13/15699; A61F 13/51498; A61F 13/539; A61F 2013/51007; A61F 13/4758;
(Continued)

(56) References Cited

U.S. PATENT DOCUMENTS 3,688,767 A * 9/1972 Goldstein .............. A41B 13/04
604/394
4,596,570 A * 6/1986 Jackson .............. A61F 13/4704
604/387

(Continued)

FOREIGN PATENT DOCUMENTS

JP 05-192367 A 8/1993
JP 3045174 Y 10/1997
(Continued)

OTHER PUBLICATIONS

International Search Report from corresponding PCT application No. PCT/JP2010/072643 dated Mar. 1, 2011 (4 pgs).
(Continued)

Primary Examiner — Paula L Craig
(74) Attorney, Agent, or Firm — Brinks Gilson & Lione

(57) ABSTRACT

A wearing article including cover sheets used to cover front and rear ends of a liquid-absorbent structure and improved to alleviate undesirable irritation due to such cover sheets potentially experienced by the wearer. A diaper includes front and rear waist members and a liquid-absorbent structure by which the front and rear waist members are connected. The liquid-absorbent structure has front and rear ends overlapping the front and rear waist members, and front and rear cover sheets are laminated on these front and rear ends to cover them. The front and rear cover sheets are formed with bonded regions adapted to be bonded to the liquid-absorbent structure or the front and rear waist members, outside non-bonded regions lying outboard of the bonded regions and inside non-bonded regions lying inboard of the bonded regions. The inside non-bonded regions are respectively folded back along fold lines toward the wearer's body to form turnbacks.

5 Claims, 4 Drawing Sheets

(58) Field of Classification Search
CPC ........ A61F 13/49466; A61F 2013/4951; A61F 2013/49493; A61F 13/495–13/496
USPC .................................. 604/365, 384, 385.201
See application file for complete search history.

(56) References Cited

U.S. PATENT DOCUMENTS

| | | | | |
|---|---|---|---|---|
| 4,670,012 A * | 6/1987 | Johnson | ................... | A61F 13/58 428/181 |
| 4,753,646 A * | 6/1988 | Enloe | ................ | A61F 13/49466 604/378 |
| 5,064,421 A * | 11/1991 | Tracy | ..................... | A61F 13/494 604/385.21 |
| 5,593,401 A * | 1/1997 | Sosalla | .............. | A61F 13/49011 604/385.28 |
| 5,690,627 A * | 11/1997 | Clear | ................. | A61F 13/15593 604/385.29 |
| 5,817,086 A * | 10/1998 | Kling | ..................... | A61F 13/495 604/385.19 |
| 5,904,675 A * | 5/1999 | Laux | ................. | A61F 13/49009 604/385.29 |
| 5,993,433 A * | 11/1999 | St. Louis | ............ | A61F 13/4942 604/385.27 |
| 6,156,022 A * | 12/2000 | Hedlund | ................ | A61F 13/495 604/385.29 |
| 6,258,076 B1 | 7/2001 | Glaug et al. | | |
| 6,491,677 B1 | 12/2002 | Glaug et al. | | |
| 6,638,262 B2 * | 10/2003 | Suzuki | ............... | A61F 13/49466 604/385.101 |
| 7,879,017 B1 * | 2/2011 | Tabata | ............... | A61F 13/49017 604/385.23 |
| 8,672,914 B2 * | 3/2014 | Ashton | ................. | A61F 13/496 604/385.201 |
| 8,945,078 B2 * | 2/2015 | Takino | ............... | A61F 13/15747 604/385.01 |
| 8,945,081 B2 * | 2/2015 | Takino | ................. | A61F 13/496 604/385.24 |
| 9,023,006 B2 * | 5/2015 | Takino | ............... | A61F 13/49011 604/385.24 |
| 9,333,122 B2 * | 5/2016 | Takino | ............... | A61F 13/49011 |
| 9,622,920 B2 * | 4/2017 | Ashton | ............... | A61F 13/49011 |
| 2001/0016720 A1 * | 8/2001 | Otsubo | ................. | A61F 13/496 604/396 |
| 2001/0049512 A1 * | 12/2001 | Kawamura | ........ | A61F 13/49466 604/312 |
| 2002/0040215 A1 | 4/2002 | Suzuki | | |
| 2002/0147438 A1 * | 10/2002 | Tanaka | .................. | A61F 13/496 604/392 |
| 2005/0027274 A1 * | 2/2005 | Suzuki | .............. | A61F 13/49001 604/385.01 |
| 2005/0175269 A1 * | 8/2005 | Ashton | .................. | A61F 13/493 385/1 |
| 2005/0182381 A1 | 8/2005 | Suzuki et al. | | |
| 2006/0047260 A1 * | 3/2006 | Ashton | ................. | A61F 13/496 604/396 |
| 2007/0142813 A1 | 6/2007 | Sperl | | |
| 2007/0203468 A1 | 8/2007 | Inoue et al. | | |
| 2010/0168703 A1 * | 7/2010 | Tange | ................... | A61F 13/496 604/365 |
| 2012/0226254 A1 * | 9/2012 | Takino | .................. | A61F 13/496 604/385.3 |

FOREIGN PATENT DOCUMENTS

| | | |
|---|---|---|
| JP | 11-318978 | 11/1999 |
| JP | 2001-037809 | 2/2001 |
| JP | 2003-500165 A | 1/2003 |
| JP | 2005-230103 | 9/2005 |
| JP | 2006-247009 A | 9/2006 |
| JP | 2007-044089 A | 2/2007 |
| WO | WO 2007/0203468 A1 | 9/2007 |

OTHER PUBLICATIONS

European Supplementary Search Report from corresponding European application No. 10840884.0 dated Jul. 3, 2014 (6 pgs).

* cited by examiner

WEARING ARTICLE

RELATED APPLICATION

This application is a 35 U.S.C. § 371 national phase filing of International Patent Application No. PCT/JP2010/072643, filed Dec. 16, 2010, through which and to which priority is claimed under 35 U.S.C. § 119 to Japanese Patent Application No. 2009-297996, filed Dec. 28, 2009.

TECHNICAL FIELD

The present invention relates to wearing articles and more particularly to the wearing articles such as disposable diapers, toilet-training pants, incontinent briefs and the like.

BACKGROUND

Conventionally, disposable diapers are known which include an absorbent structure attached to a side facing the wearer's body of a chassis formed of inner and outer sheets and the cover sheets covering front and rear ends of the absorbent structure. For example, in the disposable absorbent article disclosed in JP 2006-247009 A (PTL 1), the one end of the absorbent structure lies in the front waist region and the other end lies in the rear waist region. The respective ends are covered with the end covering sheets to prevent the ends of the absorbent structure from being put in direct contact with the wearer's skin.

CITATION LIST

Patent Literature

{PTL 1} JP 2006-247009 A

SUMMARY

Technical Problem

In the disposable absorbent article disclosed in PTL 1, the regions in which the respective end covering sheets are bonded to the absorbent structure may have unacceptably high stiffness due to an adhesive used to bonding and these regions having high stiffness may come in direct contact with the wearer's skin and may irritate the skin.

An object of the present invention is to provide a wearing article including cover sheets used to cover front and rear ends of a liquid-absorbent structure and improved to alleviate undesirable irritation due to such cover sheets potentially experienced by the wearer.

Solution to Problem

According to the present invention, there is provided a wearing article having a longitudinal direction and a transverse direction, including:
a chassis including a side facing the wearer's body, a side facing the wearer's garment, a first waist region corresponding to one of front and rear waist regions, a second waist region corresponding to the other of the front and rear waist regions and a crotch region extending between the first and second waist regions;
a liquid-absorbent structure lying on the side of the chassis facing the wearer's body and extending across the crotch region into the first and second waist regions; and
first and second cover sheets adapted to cover a first end of the liquid-absorbent structure and lying in the first waist region and a second end of the liquid-absorbent structure lying in the second waist region.

The features according to the present invention reside in that the first and second cover sheets include first and second bonded regions adapted to be bonded to the liquid-absorbent structure or the chassis and first and second non-bonded regions adjacent to an inner or outer side of the first and second bonded regions as viewed in the longitudinal direction wherein at least one of the first and second non-bonded regions is formed with a fold line extending in the transverse direction and folded back along the fold line toward the side facing the wearer's body to form a turnback.

According to one embodiment of the present invention, the first and second waist regions are bonded together along respective opposite side edges so as to form seams and the turnback is kept in a folded back state by the seams.

According to another embodiment of the present invention, the first and second cover sheets are formed of hydrophobic fibrous nonwoven fabrics.

According to still another embodiment of the present invention, the first waist region is defined by the first waist member, the second waist region is defined by the second waist member and the liquid-absorbent structure connects the first and second waist member and bonded to the side facing the wearer's body of the first and second waist members.

According to yet another embodiment of the present invention, the turnback and the first and second cover sheets are bonded together on respective sides thereof facing one another.

Advantageous Effects of Invention

According to the present invention, particularly according to one or more embodiments thereof, the wearing article has the first and second cover sheets adapted to cover the first and second ends of the liquid-absorbent structure and these first and second cover sheets are bonded to the liquid-absorbent structure or the chassis by the intermediary of the first and second bonded regions. The first and second cover sheets are formed with the first and second non-bonded regions closely adjacent to the first and second bonded regions and, at least one of the first and second non-bonded regions, the first and second cover sheets are folded back toward the wearer's body along the fold line(s) to form the turnback(s). With this unique arrangement, the turnback(s) may be sterically put in contact with the wearer's body so that the ends of the liquid-absorbent structure may be spaced from the wearer's skin and thereby possible irritation experienced by the wearer's skin may be effectively alleviated.

DESCRIPTION OF EMBODIMENTS

Details of the present invention will be more fully understood from the description of a disposable diaper as one example of the invention given hereunder with reference to the accompanying FIGS. 1 through 5.

Figure 1:
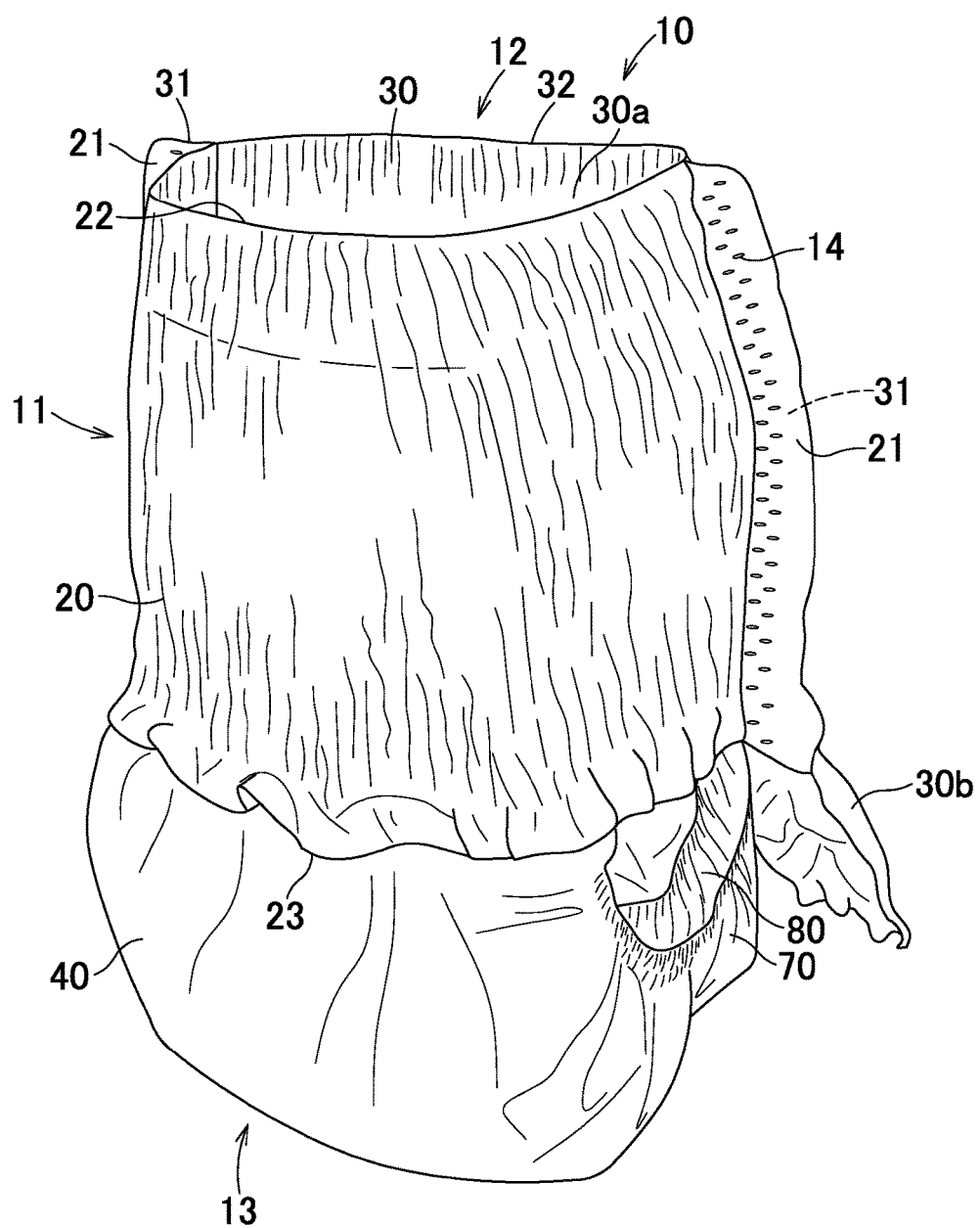
FIG. 1 is a perspective view of a diaper as one example of wearing articles.
Figure 2:
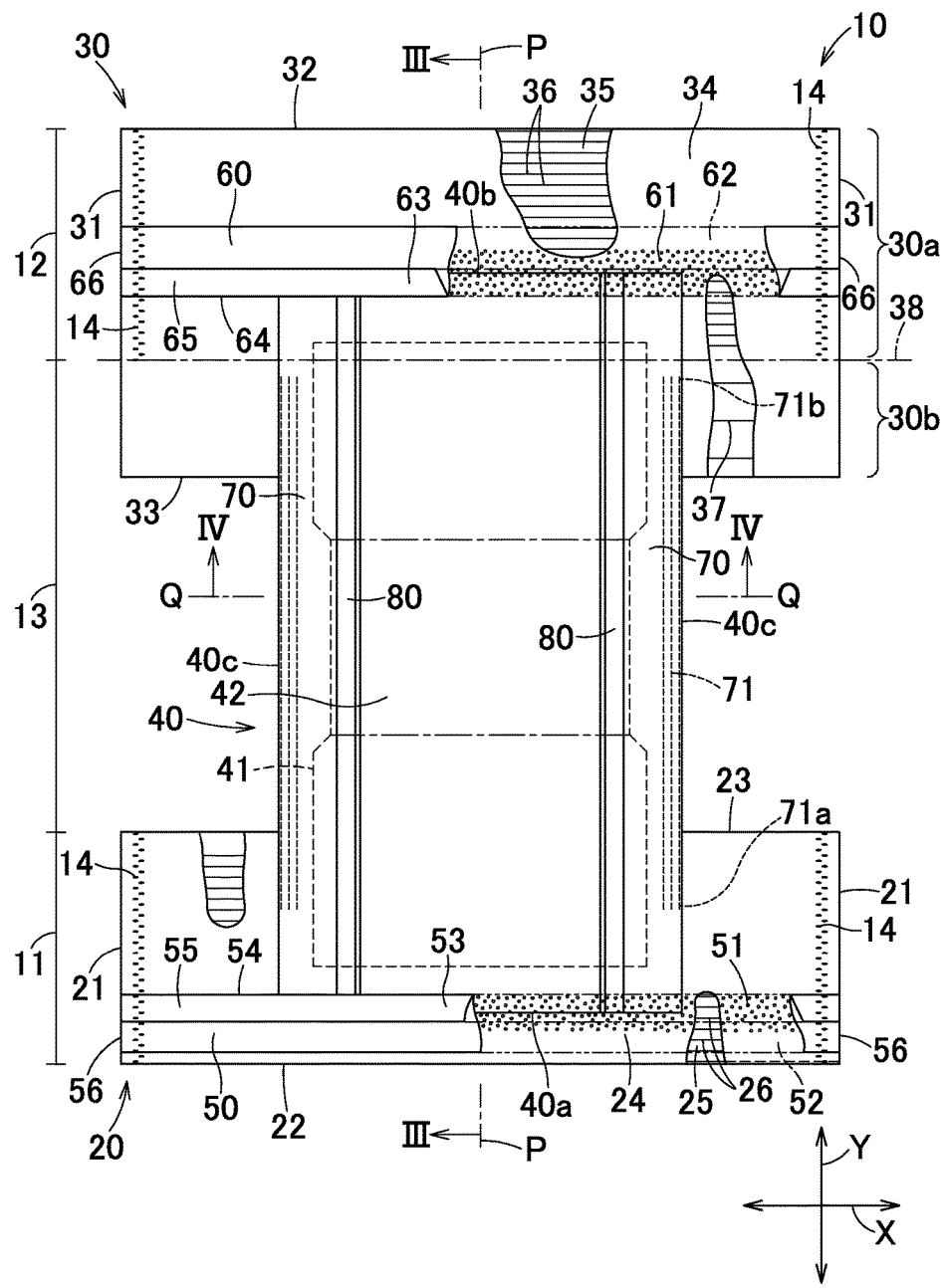
FIG. 2 is a developed plan view of the diaper.
Figure 3:
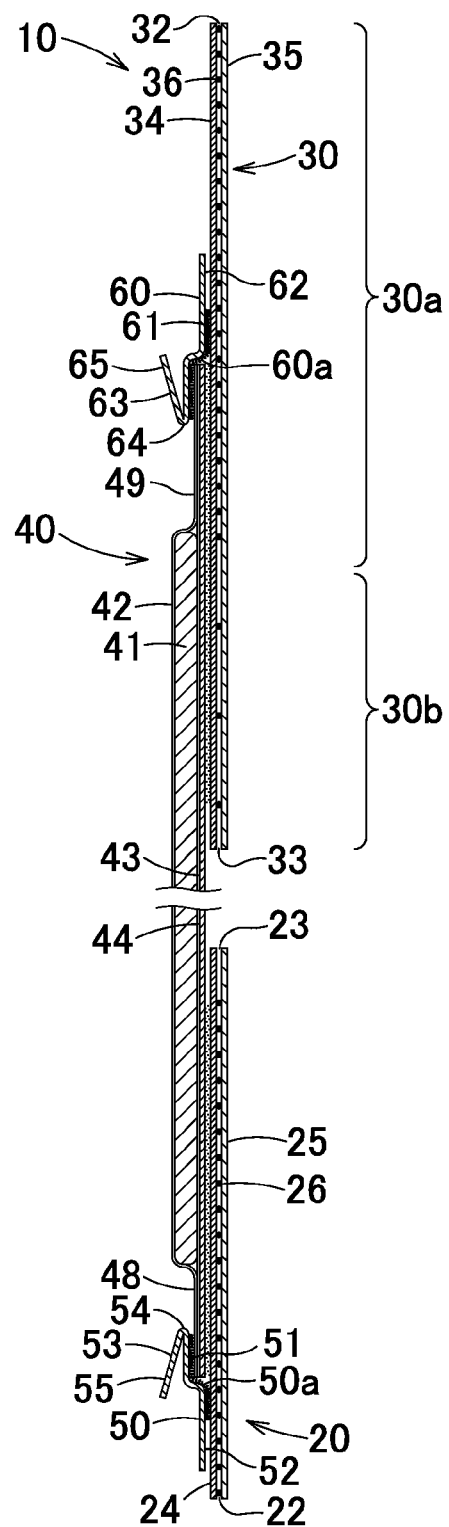
FIG. 3 is a sectional view taken along the line III-III in FIG. 2.
Figure 4:
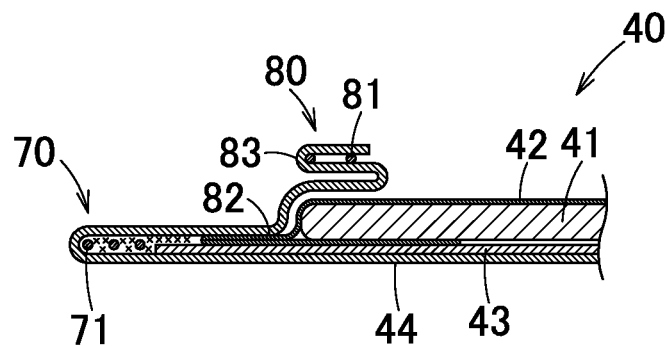
FIG. 4 is a sectional view taken along the line IV-IV in FIG. 2.
Figure 5:
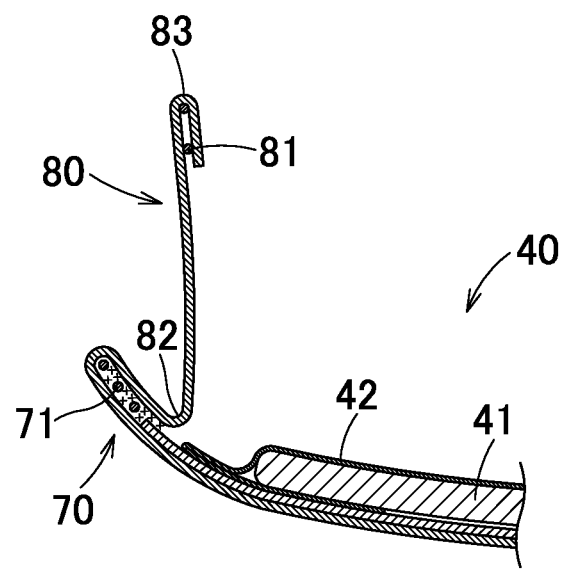
FIG. 5 is a sectional view corresponding to FIG. 4 with an associated elastic element being in a state of contraction.

FIG. 1 is a perspective view showing a diaper 10 having a waist-opening and leg-openings both kept in annular states; FIG. 2 is a developed plan view of the diaper 10 as viewed its side facing the wearer's body wherein respective elastic elements are stretched against contractile force thereof so as to maintain the diaper 10 in flattened condition; FIG. 3 is a sectional view taken along the line III-III in FIG. 2; FIG. 4 is a sectional view taken along the line IV-IV in FIG. 2; and FIG. 5 is a view similar to FIG. 4, showing the state in which the associated elastic element is a state of contraction. FIG. 2 is partially cutaway for convenience of illustration.

The diaper 10 has a longitudinal direction Y and a transverse direction X, including a side facing the wearer and a side facing the wearer's garment, a front waist region 11, a rear waist region 12 and a crotch region 13 extending between the front and rear waist regions 11, 12. The diaper 10 has an imaginary longitudinal center line P-P bisecting a dimension thereof in the transverse direction X and an imaginary transverse center line Q-Q bisecting a dimension thereof in the longitudinal direction Y. The diaper 10 has a substantially symmetric shape about the imaginary longitudinal center line P-P.

The diaper 10 includes front and rear waist members 20, spaced from each other in the longitudinal direction Y and a liquid-absorbent structure 40 connecting these front and rear waist members 20, 30 to each other and substantially defining a crotch member. The front and rear waist members 20, 30 respectively include front and rear opposite side edges 21, 31 extending in the longitudinal direction Y, first and second ends 22, 32 extending in the transverse direction X and first and second inner ends 23, 33 opposed to the first and second ends 22, 32, respectively. The front and rear opposite side edges 21, 31 are joined together to form seams 14 whereupon a waist-opening is defined by the first and second ends 22, 32 and leg-openings are defined by the inner ends 23, 33 of the front and rear waist members 20, 30 cooperating with opposite side edges 40c of the liquid-absorbent structure 40.

The rear waist member 30 is dimensioned to be longer than the front waist member 20 in the longitudinal direction Y. Specifically, the rear waist member 30 having been joined to the front waist member 20 along the side edges thereof defines a waist fit region 30a overlapping the front waist member 20 so as to cover the wearer's waist and an extension region 30b extending from the waist fit region 30a toward the crotch region 13. A border between these waist fit region 30a and the extension region 30b is defined by an imaginary line 38. The front waist member 20, i.e., the waist fit region 30a preferably has a dimension in the longitudinal direction Y in a range of about 70 to about 240 mm and of about 106 mm in the illustrated embodiment. The extension region 30b preferably has a dimension in the longitudinal direction Y in a range of about 30 to about 90 mm and of about 60 mm in the illustrated embodiment. A dimension in the transverse dimension X of the extension region 30b is substantially equal to that of the waist fit region 30a. The waist fit region 30a integrated with the extension 30b is formed of a rectangle.

A region extending from the first end 22 of the front waist member 20 to the first opposite end 23 is defined as the front waist region 11, a region extending from the second end 32 of the rear waist member 30 to the imaginary line 38, i.e., the waist fit region 30a is defined as the rear waist region 12, and a region extending from the imaginary line 38 beyond the second opposite end 33 to the first opposite end 23 is defined as the crotch region 13. The front and rear waist members 20, 30 cooperate with a part of the liquid-absorbent structure 40 to form a chassis according to the present invention.

The front and rear waist members 20, 30 respectively include front and rear inner sheets 24, 34 lying on the side facing the wearer's body, front and rear outer sheets 25, 35 lying the side facing the wearer's garment and waist elastic elements interposed between these inner and outer sheets to elasticize the front and rear waist members 20, 30 in the transverse direction X. More specifically, front and rear waist elastic elements 26, 36 each including a plurality of elastic yarns or threads and extending in the transverse direction X are attached under extension and in a contractible manner to the front waist member 20 and the waist fit region 30a. These front and rear waist elastic elements 26, 36 are arranged so as to be spaced one from another in the longitudinal direction Y preferably at an interval in a range of about 3 to about 15 mm and at an interval of about 5 mm in the illustrated embodiment. The front and rear waist elastic elements 26, 36 are arranged to have tensile stress higher in the vicinity of the first and second ends 22, 32 than in the remaining regions and thereby to assure that the waist-opening closely fits the wearer's body and body waste such as urine is prevented from leaking out of the diaper. More specifically, about 3 to 12 elastic yarns or threads each having a fineness in a range of about 470 to 1240 dtex are used as the front and rear waist elastic elements 26, 36 in a manner as follows: in the vicinity of the first and second ends 22, 32, five (5) elastic yarns or threads each having a fineness of about 470 dtex are arranged at stretching ratio of about 2.7 and, in the region placed aside from the first and second ends 22, 32 toward the crotch region 13, six (6) elastic yarns or threads each having a fineness of about 470 dtex and nine (9) elastic yarns or threads each having a fineness of 620 dtex are arranged at stretching ratio of about 2.2. The stretching ratio of the elastic yarn or thread may be appropriately varies in a range of about 1.8 to about 3.5.

The extension region 30b is provided with an extension region elastic element 37 including a plurality of elastic yarns or threads extending in the transverse direction X and attached thereto under tension and in a contractible manner. These elastic yarns or threads 37 are spaced one from another in the longitudinal direction Y preferably at an interval in a range of about 10 to about 30 mm and, in the illustrated embodiment, at an interval of about 20 mm. In any cases, the interval at which these elastic yarns or threads 37 are arranged at the large interval at which the front and rear waist elastic elements 26, 36 are arranged. It is for the reason that it is not essential for the extension region 30b to come in close contact with the wearer's body at high tensile stress. The number of the extension region elastic yarns or threads 37 may be appropriately reduced to prevent the elastic yarns or threads from disadvantageously enhancing stiffness of the extension region 30b. As the extension region elastic yarns or threads 37, the elastic yarns or threads each having a fineness in a range of about 470 to 1240 dtex may be attached to the extension region 30b at stretching ratio in a range of about 1.5 to about 3.2. In the illustrated embodiment, as the extension region elastic element 37, three (3) elastic yarns or threads each having a fineness of about 470 dtex may be used and attached to this region 30b at stretching ratio of about 2.2.

The respective elastic elements 26, 36, 37 may be directly coated therearound with a hot melt adhesive or the like to be bonded to the front inner and outer sheets 24, 25 or the rear inner and outer sheets 34, 35 and thereby to bond the front inner and outer sheets 24, 25 to the rear inner and outer sheets 34, 35. Consequentially, it is surely avoided that the elastic elements might fall off and a surplus amount of the adhesive might enhance stiffness of the sheets.

The liquid-absorbent structure 40 includes a liquid-absorbent core 41, an inner sheet 42 lying on the side facing the wearing body to cover an absorbent surface of the core 41, a leakage-barrier sheet 43 cover a bottom of the core 41 and an outer sheet 44 covering a bottom surface of the leakage-barrier sheet 43. These inner and outer sheets 42, 44 define a cover sheet for the core 41. As the core 41, fluff pulp fibers, super-absorbent polymer particles or the like may be used.

As the inner sheet 42, a liquid-pervious fibrous nonwoven fabric or the like may be used. For example, a hot air-through fibrous nonwoven fabric, a point-bonded fibrous nonwoven fabric or a spun bonded fibrous nonwoven fabric each having a basis mass in a range of about 10 to about 30 g/m$^2$ may be used.

As the leakage-barrier sheet 43, a moisture-pervious but liquid-impervious plastic film may be used so that this sheet 43 may cover at least the entire bottom surface of the liquid-absorbent structure 41 and thereby may prevent body waste such as urine from leaking out of the diaper 10.

As the outer sheet 44, for example, a spun bonded/melt blown/spun bonded (SMS) fibrous nonwoven fabric, a point-bonded fibrous nonwoven fabric or a spun bonded fibrous nonwoven fabric each having a basis mass in a range of about 10 to about 25 g/m$^2$ may be used.

The inner sheet 42, the leakage-barrier sheet 43 and the outer sheet 44 of the liquid-absorbent structure 40 are dimensioned to be larger than the dimension of the core 41 in the longitudinal direction Y. In the vicinities of front and rear ends 40a, 40b of such liquid-absorbent structure 40, the core 41 is not present so that front and rear end flaps 48, 49 are formed of the inner sheet 42, the leakage-barrier sheet 43 and the outer sheet 44. In these front and rear end slaps 48, 49, the inner sheet 42, the leakage-barrier sheet 43 and the outer sheet 44 are directly bonded to one another by bonding means such as hot melt adhesives (it is also possible to bond indirectly these sheets to one another without departing from the scope of the present invention).

In the transverse direction X also, the inner sheet 42, the leakage-barrier sheet 43 and the outer sheet 44 extend outward beyond the side edges of the core 41 and these sheets are directly bonded to one another with an adhesive such as a hot melt adhesive (it is also possible to bond indirectly these sheets to one another without departing from the scope of the present invention). Outboard of the liquid-absorbent structure 40 in the transverse direction X, the outer sheet 44 forms gasket cuffs 70 and leakage-barrier cuffs 80. The outer sheet 44 extending outward in the transverse direction X beyond the opposite side edges of the core 41 are folded back to form the gasket cuffs 70. Each of the gasket cuffs 70 has a dimension of about 35 mm in the transverse direction X as measured outside front and rear regions 45, 46 of the core 41 and of about 75 mm in the transverse direction X as measured outside a middle region 47 of the core 41.

In the folded back side edge of the outer sheet 44, each of the gasket cuffs 70 sandwiches two or more gasket cuff elastic elements 71 extending in the longitudinal direction Y and attached thereto under tension and in a contractible manner so that the gasket cuff 70 may be elasticized in the longitudinal direction Y. As the gasket cuff elastic element 71, elastic yarn or thread having a fineness in a range of about 470 to about 1240 dtex may be attached at a stretching ratio in a range of about 2.3 to about 3.0. In the illustrated embodiment, three (3) elastic yarns or threads each having a fineness of about 620 dtex are used as the gasket cuff elastic elements 71 and attached at stretching ratio of about 2.8. In each of the gasket cuffs 70, the outer sheet 44, the leakage-barrier sheet 43 and the gasket cuff elastic elements 71 are bonded to one another by bonding means such as adhesives. Each of the gasket cutoff elastic elements 71 has its one end 71a overlapping a part of each of the front waist elastic elements 26 and its other end overlapping a part of each of the extension region elastic elements 37 (See FIG. 2).

As will be apparent from FIGS. 4 and 5, each leakage-barrier cuff 80 includes a proximal edge 82 lying on the inner side as viewed in the transverse direction X and extending in the longitudinal direction Y and a distal edge 83 lying on the outer side as viewed in the transverse direction X and extending in the longitudinal direction Y. Each of the leakage-barrier cuffs 80 is formed by folding a portion of the outer sheet 44 extending inward from the associated gasket cuff 70 and lies above the liquid-absorbent structure 40. By folding back the outer sheet 44 in this manner, the distal edges 83 lie in the vicinity of the opposite side edges 41c of the core 41 and the proximal edges 82 lie on the side of the core 41 facing the wearer's body.

Each of the distal edges 83 is provided with two or more barrier cuff elastic elements 81 extending in the longitudinal direction Y and attached thereto under tension and in a contractible manner to elasticize the barrier cuffs 80 in the longitudinal direction Y. Being elasticized in this fashion, the respective distal edges 83 are spaced upward from the inner sheet 42 as illustrated in FIG. 5 with the diaper 1 put on the wearer's body to form the leakage-barrier cuffs 80. As the leakage-barrier cuff elastic elements 81, elastic yarns or threads each having a fineness in a range of 470 to about 1240 dtex may be attached at stretching ratio in a range of about 2.3 to about 3.0. In the illustrated embodiment, two (2) elastic yarns or threads each having a fineness of about 620 dtex are used and attached at stretching ratio of about 2.8.

The liquid-absorbent structure 40 has its front and rear ends 40a, 40b overlapping the front and rear waist members 20, 30, respectively, and front and rear cover sheets 50, 60 are laminated thereon to cover the front and rear ends 40a, 40b (See FIGS. 2 and 3). The front and rear cover sheets 50, 60 extend in the transverse direction X to have respective opposite side edges 56, 66 coinciding with the respective opposite side edges 21, 31 of the front and rear waist members 20, 30 and thereby to cover the entire area of the front and rear ends 40a, 40b of the liquid-absorbent structure 40. By covering the front and rear ends 40a, 40b with the front and rear cover sheets 50, 60, respectively, it is ensured to prevent the component material of the core 41 from falling off and, in addition, to protect the wearer against suffering from skin trouble due to contact of the front and rear ends 40a, 40b with the wearer's skin.

As the front and rear cover sheets 50, 60, a hydrophobic but breathable fibrous nonwoven fabric may be used. For example, a hot air-through fibrous nonwoven fabric, a point-bonded fibrous nonwoven fabric or a spun bonded fibrous nonwoven fabric which have not been modified to become hydrophilic may be used. It should be understood here that hydrophilic front and rear cover sheets 50, 60 may be used without departing from the scope of the present invention.

The front and rear cover sheets 50, 60 are formed on surfaces 50a, 60a thereof facing the front and rear waist members 20, 30, respectively, with bonded regions 51, 61 adapted to be bonded to the liquid-absorbent structure 40 or the front and rear waist member 20, 30 by bonding means such as hot melt adhesives. Immediately outside these bonded regions 51, 61 as viewed in the longitudinal direction Y, outboard of non-bonded regions 52, 62 are formed and, immediately inboard of the bonded regions 51, 61 as viewed in the longitudinal direction Y, inside non-bonded regions 53, 63. These non-bonded regions 52, 62; 53, 63 are free to be spaced from the liquid-absorbent structure 40 or the front and rear waist members 20, 30, respectively.

The inside non-bonded regions 53, 63 are formed with fold lines 54, 64. The front and rear cover sheets 50, 60 are folded back toward the side facing the wearer's body along these fold lines 54, 64 to form turnbacks 55, 65. The fold lines 54, 64 are respectively formed along borders between the bonded regions 51, 61 and the inside non-bonded regions 53, 63. The fold lines 54, 64 respectively extend the opposite side edges 55, 55 and 65, 65 along which the respective turnbacks 55, 65 are formed. These turnbacks 55, 65 are respectively bonded to the front and rear waist members 20, 30 by the seams 14. Consequently, the turnbacks 55, 65 are maintained in turned back states at least in the vicinity of the respective opposite side edges 56, 66.

The turnbacks 55, 65 of the respective cover sheets 50, 60 are adapted to raise themselves toward the wearer's body under the effect of the sheets' stiffness in segments thereof other than the respective segments in the vicinity of the side edges 56, 66. With the diaper put on the wearer's body, therefore, the turnbacks 55, 65 are kept in contact with the wearer's body and the front and rear ends 40a, 40b of the liquid-absorbent structure 40 are spaced from the wearer's skin. Along the front and rear ends 40a, 40b of the liquid-absorbent structure 40, two or more sheets are laminated one on another and bonded together with an adhesive. Inevitably such adhesive enhances stiffness along these front and rear ends 40a, 40b. However, these front and rear ends 40a, 40b are adapted to be spaced from the wearer's skin and these front and rear ends 40a, 40b should not irritate the wearer's skin.

The turnbacks 55, 65 may raise themselves on the liquid-absorbent structure 40 and come in close contact with the wearer's skin and thereby can faction as leakage-barriers against body waste such as urine. In addition, the formation of the bonded regions 51, 61 extending in the transverse direction X makes it possible to prevent body waste such as urine from leaching toward the waist-opening.

While the turnbacks 55, 65 are formed along both the inside non-bonded regions 53, 63 of the front and rear cover sheets 50, 60, it is also possible without departing from the scope of the invention to form the turnback at least in one of the inside non-bonded regions 53, 63 or at least in one of the outside non-bonded regions 52, 62. It is also possible without departing from the scope of the invention to coat the regions not turned back with adhesives to form the bonded regions instead of leaving them as the non-bonded regions.

As the front and rear cover sheets 50, 60, hydrophobic and water-repellent sheets are used and thereby leaching out of body waste such as urine from the side of the liquid-absorbent structure 40 toward the waist-opening can be prevented. By forming the front and rear cover sheets 50, 60 with the turnbacks 55, 65 so that the turnbacks 55, 65 may be closely laminated with the main bodies of the cover sheets 50, 60, leaching out of body waste such as urine can further reliably prevented.

While the turnbacks 55, 65 are bonded to the main bodies of the front and rear cover sheets 50, 60 by the seams 14 only in the vicinity of the opposite side edges thereof in the illustrated embodiment, it is possible without departing from the scope of the invention to bond the turnbacks 55, 65 as a whole or partially to the main bodies of the front and rear cover sheets 50, 60. In this way, these sheets can be closely laminated with each other.

The terms "first" and "second" used in the specification and claims of the present invention are used should merely to discriminate identical elements, positions etc. The term "first waist region" used in the specification and claims of the present invention means one of the front and rear waist regions and the term "second waist region" means the other waist region.

REFERENCE SIGNS LIST 10 diaper (wearing article)
11 front waist region (first or second waist region)
12 rear waist region (first or second waist region)
13 crotch region
14 seams
20 front waist member (first or second waist member)
21 front opposite side edges
30 rear waist member (first or second waist member)
31 rear opposite side edges
40 liquid-absorbent structure
40a front end (first or second end)
40b rear end (first or second end)
50 front cover sheet (first or second cover sheet)
60 rear cover sheet (first or second cover sheet)
51 bonded region (first or second bonded region)
52 outside non-bonded region (first or second non-bonded region)
53 inside non-bonded region (first or second non-bonded region)
54 fold line
55 turnback
61 bonded region (first or second bonded region)
62 outside non-bonded region (first or second non-bonded region)
63 inside non-bonded region (first or second non-bonded region)
64 fold line
65 turnback
X transverse direction
Y longitudinal direction

The invention claimed is:

1. A wearing article having a longitudinal direction and a transverse direction, comprising:
    a chassis comprising a side facing the wearer's body, a side facing the wearer's garment, a first waist region corresponding to one of front and rear waist regions, a second waist region corresponding to the other of the front and rear waist regions and a crotch region extending between the first and second waist regions;
    a liquid-absorbent structure lying on the side of the chassis facing the wearer's body and extending across the crotch region into the first and second waist regions, said liquid-absorbent structure including a liquid-absorbent core;
    a waist opening and a pair of leg openings; and
    first and second cover sheets that are each spaced apart from the waist opening, the first cover sheet is adapted to cover a first end of the liquid-absorbent structure and lying in the first waist region and the second cover sheet is adapted to cover a second end of the liquid-absorbent structure lying in the second waist region, wherein:
    the first cover sheet includes a first bonded region extending in the transverse direction over a greater distance than in the longitudinal direction and is adapted to be bonded to the liquid-absorbent structure or the chassis and a first non-bonded region adjacent to an inner or outer side of the first bonded region as viewed in the longitudinal direction, the second cover sheet includes a second bonded region extending in the transverse direction over a greater distance than in the longitudinal direction and is adapted to be bonded to the liquid absorbent structure or the chassis and a second non-bonded region adjacent to an inner or outer side of the second bonded region as viewed in the longitudinal direction, wherein at least one of the first and second non-bonded regions is formed with a fold line extending in the transverse direction and folded back along the fold line toward the side facing the wearer's body to form a turnback which turnback does not overlap the liquid-absorbent core, each of the first and second waist regions has waist elastic elements including a plurality of elastic yarns or threads and extending in the transverse direction which are attached under extension and in a contractible manner thereto, and the first and second waist regions are bonded together along respective opposite side edges so as to form seams and the turnback is kept in a folded back state by the seams.

2. The wearing article defined by claim 1, wherein each of the first and second cover sheets is formed of hydrophobic fibrous nonwoven fabric.

3. The wearing article defined by claim 2, wherein the first waist region is defined by a first waist member, the second waist region is defined by a second waist member and the liquid-absorbent structure connects the first and second waist member and bonded to the side facing the wearer's body of the first and second waist members.

4. The wearing article defined by claim 1, wherein the first waist region is defined by a first waist member, the second waist region is defined by a second waist member and the liquid-absorbent structure connects the first and second waist member and bonded to the side facing the wearer's body of the first and second waist members.

5. The wearing article defined by claim 1, wherein the turnback is bonded to a portion of one of the first cover sheet that is over the first bonded region or is bonded to a portion of the second cover sheet that is over the second bonded region.

* * * * *